United States Patent [19]

Goleczka et al.

[11] Patent Number: 4,643,977

[45] Date of Patent: Feb. 17, 1987

[54] PROCESS FOR ASSESSING COKE MICRO-REACTIVITY

[75] Inventors: Joseph Goleczka; Edmund P. Mills, both of Cheltenham; Edward K. Harrison, Retford; Roy Nichols, Rowlands Gill, all of England

[73] Assignee: Coal Industry (Patents) Limited, England

[21] Appl. No.: 710,217

[22] Filed: Mar. 11, 1985

[51] Int. Cl.⁴ .............................................. G01N 33/00
[52] U.S. Cl. ......................................... 436/34; 201/1; 436/145; 436/155
[58] Field of Search .................... 201/1, 41, 43, 24, 42, 201/8; 423/449, 460; 422/78; 436/34, 145, 155

[56] References Cited

PUBLICATIONS

Hyslop, W., "Carbon Solution and Coke Quality", *The Coke Oven Managers' Year-Book*, 1981, pp. 131–152.

Brown, F., "Developments in Coal Blending and Coke Quality at the British Steel Corporation's Teesside Works", *The Coke Oven Manager's Year-Book*, 1980, pp. 87–105.

Lowry, *Chemistry of Coal Utilization*, vol. 1 (1945), pp. 912–917.

Primary Examiner—Barry S. Richman
Assistant Examiner—Joye Woodard
Attorney, Agent, or Firm—Stevens, Davis, Miller & Mosher

[57] ABSTRACT

Micro-reactivity of cokes can be estimated by carbonizing a small sample of powdered coal to form a char and until constant weight at a desired test temperature, then measuring weight loss in a given time.

6 Claims, 1 Drawing Figure

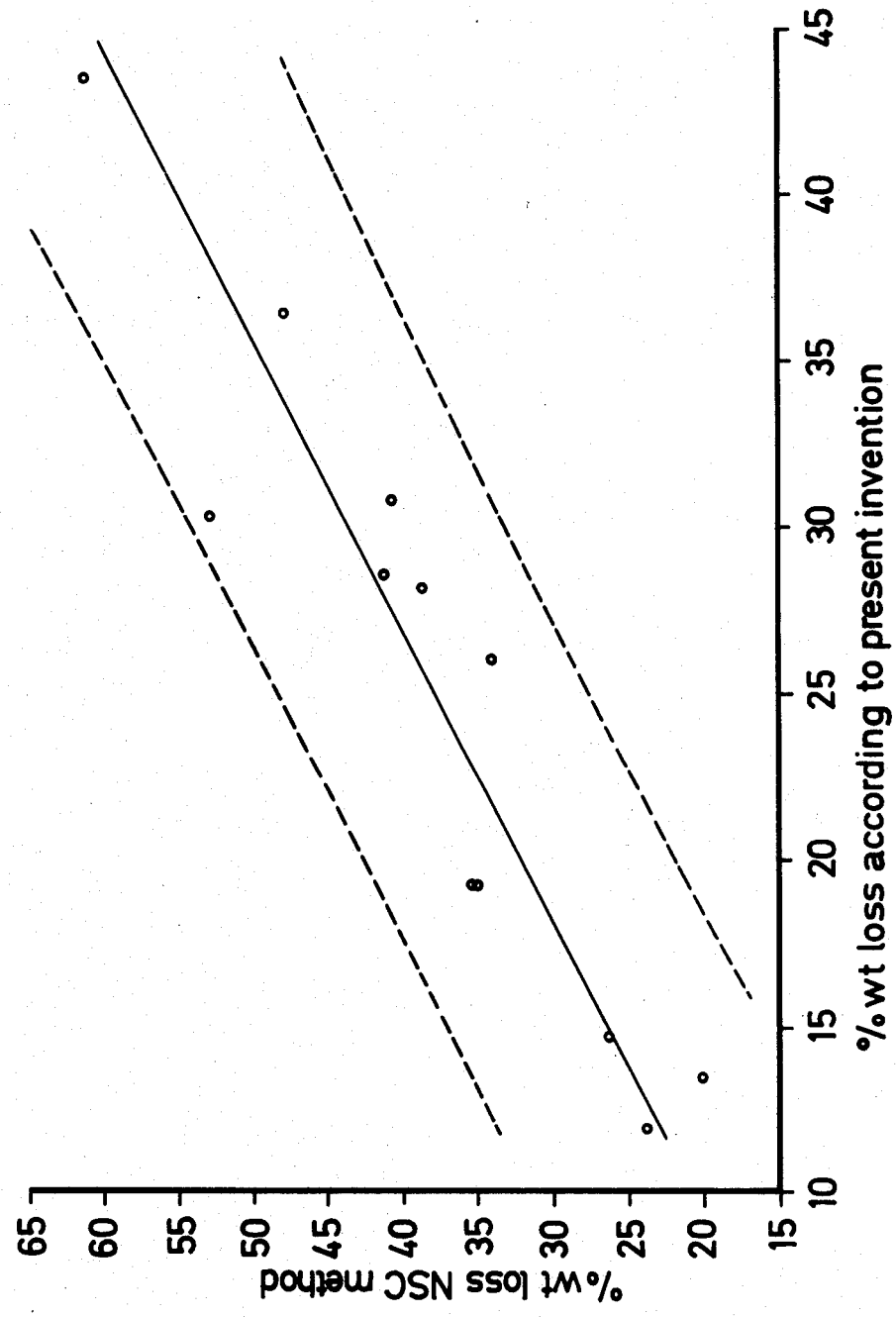

PROCESS FOR ASSESSING COKE MICRO-REACTIVITY

BACKGROUND OF THE INVENTION

This invention concerns a coal carbonisation test, more especially it concerns a test which gives information on coke micro-reactivity.

Considerable attention is currently being paid to the reactivity to carbon dioxide of carbonised coals or cokes. A favoured test for the reactivity of coke is the Nippon Steel Corporation (NSC) method (COMA Yearbook 1980, 87), involving determining the percentage weight loss of a 200 g sample of a closely sized lump coke (20±1 mm) in carbon dioxide at 1100° C. for 2 hours. A special standard apparatus has been devised for carrying out the NSC method; not only is the apparatus expensive but the method is time-consuming and labour-intensive. Thus to assess a coal or coal blend for commencial use, test cokes have to be prepared and this requires up to one day. Thereafter, the method itself requires skilled laboratory personnel. It would be of considerable assistance to coke oven plant operators if a simpler, quicker and cheaper test could be devised capable of being carried out by relatively unskilled personnel at the plant and enabling plant management to predict and monitor the likely performance of a coal feed or blend on the commercial scale before coke is actually made. It would be most advantageous if any test method could be found to bypass the need to make test cokes in a test or pilot oven. We believe that we have found a quick and simple method which avoids most if not all of the drawbacks of the NSC method, yet gives results which correlate very well with those of the NSC method.

SUMMARY OF THE INVENTION

Accordingly, the present invention provides a method for assessing the micro-reactivity of coke, which comprises taking a small representative sample of a finely divided coal or coal blend, carbonising if under an inert gas by heating until a constant weight is obtained at the desired reactivity test temperature, passing carbon dioxide over the carbonised sample at the desired test temperature and measuring the weight loss in a given time.

It can be seen at once that the starting material for the method of the invention is not a coke but a coal. We do not believe that this has previously been suggested although it offers particular advantages which will become clearer hereinafter. The coal or coal blend is preferably ground or crushed to a suitable size; for example in tests which are found to give good correlation with the NSC method a suitable size range is 72–120 BS sieve sizes (212–125 $\mu$m), which is within a size range frequently prepared in the UK industry for proximate analysis of the feed coal(s). The weight of the sample is not critical to the present invention, the successful tests have been carried out with as little as 150 mg of coal, although it is envisaged that a test method suitable for plant use would use about 10 g. However, it is important to ensure that the sample is representative, and known methods exist for sampling to give a statistically representative sample, normally involving a riffling procedure.

BRIEF DESCRIPTION OF THE DRAWINGS

The accompanying single FIGURE of drawings is a graph comparing results of the present invention with that of the NSC method.

DESCRIPTION OF A PREFERRED EMBODIMENT

The coal or blend sample is heated to a preselected temperature under an inert gas, preferably under a stream of the gas which is conveniently nitrogen, although any inert gas may be used. The preselected temperature would normally be in the range 900° to 1200° C., and in the NSC method is 1100° C. The rate of heating is also conveniently that met with in conventional carbonisation in an oven, of the order of 5° C./min. It may be possible, if desired, to speed up the test by heating at a faster rate, especially in the post-plastic phase above about 500° C., but because the method can operate with small samples the problems of bulk heating are avoided, and carbonisation times are of the order of 3½ hours instead of 17–20 hours in coke ovens. If the coal(s) being tested are strongly caking, it is desirable to physically separate the individual particles of coal to prevent agglomeration. Since the method of the invention is a micro-reactivity test and not intended to simulate or give information on coke bulk reactivity, it is necessary only to form a char rather than a coke in which fusion has taken place.

The reaction of the carbonised sample with carbon dioxide is suitably carried out by passing a stream of $CO_2$ over the sample. Preferably, the weight of the sample is constantly monitored against time, but the sample may be weighed before and after a known period of $CO_2$ treatment. The NSC method specifies weighing before and after passing $CO_2$ for 2 hours; we have found that the $CO_2$ treatment may be carried out until a 20% weight loss or for a fixed time since weight loss is linear with time, providing that the same procedure is used for comparisons.

Preferably, the method of the invention is carried out in a furnace in which the sample of coal or blend can be heated and exposed to, in turn, the inert gas and $CO_2$, and in which the sample can be weighed continuously or at the necessary points in the procedure.

We have also noted that there is a closely linear relationship between NSC reactivity results and post-reaction strengths (involving the tumbling of a coke which has undergone reaction with $CO_2$, under standard conditions and measuring the breakage). Accordingly, we believe that the method of the present invention can be used to give useful information on post reaction strength as well as micro-reactivity.

The invention will now be described by way of example only.

EXAMPLE

Representative samples of a variety of coals and coal blends were crushed and sieved to yield finely divided coal in the size range 212–125 $\mu$m and 150 mg samples were carefully taken. The samples were placed in the sample holder of a commercial thermobalance and then heated under flowing nitrogen (400 ml/min) at 5° C./min to the temperature at which the reactivity measurements were to be made, 1100° C. The thermobalance provides a continuous reading of weight and when the temperature and weight of the sample had stabilised, the nitrogen was replaced by $CO_2$ for 10 minutes. Each test could be completed within 4 hours, compared to at least one day normally required to carry out the NSC method by coking in a pilot oven then carrying out the NSC specified procedures.

For comparison purposes, the same coals and blends were coked in a 250 kg pilot oven by crushing the raw coal so that 85% passed through 3.35 mm screen and charging to the oven in the wet state (9% moisture). The pilot oven was gas heated, the flue side of the walls being maintained at 1180° C. After 17 hours nominal carbonisation time, the charge was discharged and water quenched. The charge centre temperature was about 1030° C. upon discharge. 200 g samples of the resulting cokes were tested in accordance with the NSC method.

The results of NSC reactivity and micro-reactivity according to the present invention are plotted in the accompanying FIGURE. The slope of the best straight line gives an equation:

$$NSC\ reactivity = 1.152\ MR + 9.050$$

where MR is the % weight loss after 10 minutes in the method of the invention as described above.

A correlation coefficient of 0.936 is found, and we believe that the method offers a valuable alternative to the NSC method.

While the method of the invention describes specifically an alternative to the NSC method, it is believed that the invention offers alternatives to many other reactivity tests carried out at local level to assess cokes and carbonised solid fuels of many types.

We claim:

1. A method for assessing the micro-reactivity of a solid carbonized residue which does not exhibit significant agglomeration, formed from a coal or coal blend, comprising the steps of:
   (a) carbonizing a small, finely divided representative sample of the coal or coal blend under an inert gas by heating until a constant weight is obtained at a desired reactivity test temperature and to form the solid carbonized residue which does not exhibit significant agglomeration; and
   (b) passing carbon dioxide over the carbonized residue at the desired test temperature and measuring a weight loss in a given time whereby the weight loss is a measure of the micro-reactivity of coke formed from the same coal or coal blend.

2. A method as claimed in claim 1, wherein the coal or coal blend sample is of a particle size in the range 125–212 μm.

3. A method as claimed in claim 1, wherein the test temperature is in the range 900° to 1200° C.

4. A method as claimed in claim 1, wherein the sample is heated at a rate of approximately 5° C./min.

5. A method as claimed in claim 1, wherein the sample is weighed continuously in the heating and the carbon dioxide treatment steps.

6. A method as claimed in claim 5, wherein the heating and carbon dioxide treatment steps are carried out in a thermobalance.

* * * * *